United States Patent
Gough et al.

(10) Patent No.: US 8,900,385 B2
(45) Date of Patent: Dec. 2, 2014

(54) COMPOSITE FOR ON DEMAND FRAGRANCE DELIVERY AND RELATED METHOD OF MANUFACTURE

(75) Inventors: Christopher Gough, Winnetka, CA (US); Margaret Hyde, Winnetka, CA (US); Timothy Thomson, West Newbury, MA (US)

(73) Assignee: Mo's Nose LLC

( * ) Notice: Subject to any disclaimer, the term of this patent is extended or adjusted under 35 U.S.C. 154(b) by 526 days.

(21) Appl. No.: 13/022,603

(22) Filed: Feb. 7, 2011

(65) Prior Publication Data

US 2011/0194983 A1   Aug. 11, 2011

Related U.S. Application Data

(60) Provisional application No. 61/337,704, filed on Feb. 8, 2010.

(51) Int. Cl.
*A62B 7/08*   (2006.01)
*B29C 65/48*   (2006.01)
(Continued)

(52) U.S. Cl.
CPC ............... *B32B 37/206* (2013.01); *A61L 9/042* (2013.01); *B32B 3/28* (2013.01); *B32B 3/085* (2013.01); *C09J 2467/006* (2013.01); *B29C 66/131* (2013.01); *C09J 2423/00* (2013.01); *B29C 2791/006* (2013.01); *C09J 2201/20* (2013.01); *C09J 2483/005* (2013.01); *C09J 2467/00* (2013.01); *B29C 66/112* (2013.01); *A45D 40/0087* (2013.01); *C09J 2423/006* (2013.01); *C09J 7/0296* (2013.01); *B29C 51/10* (2013.01); *B32B 2266/025* (2013.01);
(Continued)

(58) Field of Classification Search
CPC .................................... B32B 9/00; A62B 7/48
USPC .............................. 156/87; 422/123
See application file for complete search history.

(56) References Cited

U.S. PATENT DOCUMENTS 4,161,284 A   7/1979 Rattan
4,226,944 A   10/1980 Stone et al.
(Continued)

FOREIGN PATENT DOCUMENTS

EP   1914260   2/1991
EP   1914269   4/2008
(Continued)

OTHER PUBLICATIONS

Yokota et al., Method and Apparatus for Impregnating Sponge Like Element With Liquid, Mar. 5, 1996, JP 08058213 A, English Abstract.*

(Continued)

*Primary Examiner* — Margaret Squalls
(74) *Attorney, Agent, or Firm* — Onofrio Law; Dara L. Onofrio, Esq

(57) ABSTRACT

A composite for on demand release of fragrance, comprising a foam layer imbibed with fragrance; a top polymer layer, impermeable to said fragrance but containing perforations; and a bottom double sided film adhesive layer with a releaser liner on the outside surface; such that said foam layer is in between said top and bottom layer and when compressed by a user said fragrance is released thru the perforations in said top layer. Related method of manufacture and use of the composites in a book are also provided.

6 Claims, 3 Drawing Sheets

(51) Int. Cl.

| | | |
|---|---|---|
| *A61L 9/04* | (2006.01) | |
| *B32B 3/28* | (2006.01) | |
| *B32B 3/08* | (2006.01) | |
| *A45D 40/00* | (2006.01) | |
| *B32B 37/20* | (2006.01) | |
| *C09J 7/02* | (2006.01) | |
| *B32B 7/12* | (2006.01) | |
| *B32B 5/18* | (2006.01) | |
| *A45D 37/00* | (2006.01) | |
| *B32B 38/00* | (2006.01) | |
| *B32B 27/40* | (2006.01) | |
| *B32B 27/36* | (2006.01) | |
| *B32B 3/04* | (2006.01) | |
| *B32B 27/32* | (2006.01) | |
| *B32B 3/26* | (2006.01) | |
| *C11D 3/50* | (2006.01) | |
| *B32B 29/00* | (2006.01) | |
| *B32B 27/10* | (2006.01) | |
| *B32B 27/06* | (2006.01) | |
| *B29C 65/00* | (2006.01) | |
| *B29C 51/10* | (2006.01) | |
| *B32B 37/24* | (2006.01) | |

(52) U.S. Cl.
CPC ............ B32B 2260/04 (2013.01); *B32B 7/12* (2013.01); *B29C 2793/009* (2013.01); *B32B 5/18* (2013.01); *B32B 2260/02* (2013.01); *A45D 37/00* (2013.01); *B32B 38/0004* (2013.01); *B32B 2309/105* (2013.01); *B32B 2250/03* (2013.01); *C09J 2400/243* (2013.01); *B32B 27/40* (2013.01); *B32B 2266/0278* (2013.01); *B32B 27/36* (2013.01); *B32B 2405/00* (2013.01); *B32B 3/04* (2013.01); *B32B 27/32* (2013.01); *B32B 2037/243* (2013.01); *C09J 2475/006* (2013.01); *C09J 2475/00* (2013.01); *B32B 2305/022* (2013.01); *B32B 3/266* (2013.01); *B29C 66/53461* (2013.01); *C11D 3/505* (2013.01); *B32B 29/007* (2013.01); *C09J 2400/226* (2013.01); *B32B 27/10* (2013.01); *B29C 2791/001* (2013.01); *B32B 27/065* (2013.01)
USPC ............................................ 156/87; 156/60

(56) References Cited

U.S. PATENT DOCUMENTS

| | | | |
|---|---|---|---|
| 4,254,179 A | | 3/1981 | Carson, III et al. |
| 4,257,176 A | | 3/1981 | Hartung et al. |
| 4,277,024 A | * | 7/1981 | Spector ........................ 239/36 |
| 4,339,550 A | | 7/1982 | Palinczar |
| 4,419,396 A | | 12/1983 | Sugimoto |
| 4,493,869 A | | 1/1985 | Sweeny et al. |
| 4,584,281 A | | 4/1986 | Foley |
| 4,657,625 A | * | 4/1987 | Kawakami .................... 156/471 |
| 4,858,831 A | | 8/1989 | Spector |
| 4,880,690 A | | 11/1989 | Szycher et al. |
| 5,098,621 A | | 3/1992 | Hermann |
| 5,314,325 A | * | 5/1994 | Bosler ......................... 425/384 |
| 5,391,420 A | * | 2/1995 | Bootman et al. ............ 206/213.1 |
| 6,147,037 A | | 11/2000 | Gardlik et al. |
| 6,254,836 B1 | | 7/2001 | Fry |
| 6,326,069 B1 | | 12/2001 | Barnett |
| 6,536,635 B1 | | 3/2003 | Garcia et al. |
| 6,663,019 B2 | | 12/2003 | Garcia et al. |
| 6,736,335 B2 | | 5/2004 | Cuthbert |
| 6,752,298 B2 | | 6/2004 | Garcia et al. |
| 7,682,575 B2 | | 3/2010 | Hurwitz et al. |
| 7,815,878 B1 | | 10/2010 | Wheatley |
| 2006/0013963 A1 | | 1/2006 | Thomson |
| 2006/0062700 A1 | | 3/2006 | Hurwitz et al. |
| 2008/0279730 A1 | | 11/2008 | Triplett |
| 2009/0081912 A1 | | 3/2009 | Burrow et al. |
| 2009/0151728 A1 | | 6/2009 | McConnell et al. |
| 2009/0162408 A1 | | 6/2009 | SenGupta |
| 2010/0205799 A1 | | 8/2010 | Alticosalian |
| 2011/0000873 A1 | | 6/2011 | Dobler |

FOREIGN PATENT DOCUMENTS

| | | | |
|---|---|---|---|
| JP | 08058213 A | * | 3/1996 |
| WO | WO 02083043 | | 10/2002 |

OTHER PUBLICATIONS

"DiscCover—Fine Fragrance" Arcade Marketing, 2011 http://www.arcadeinc.com/categories/technology/fine-fragrance/disccover.html.

"Squeeze Mist" Emsar, www.emsargroup.com http://www.emsargroup.com/pdf/Sgueeze%20Mist%20inch.pdf, Feb. 7, 2011.

Mecofoam by Prameco Co., Ltd http://www.ecplaza.net/product/108834_402063/perfumed_jewelry.html, Feb. 7, 2011.

Article entitled "MIT microchip releases chemicals on demand" MIT News Office (Jan. 27, 1999); http://web.mit.edu/newsoffice/nr/1999/microchip.html.

* cited by examiner

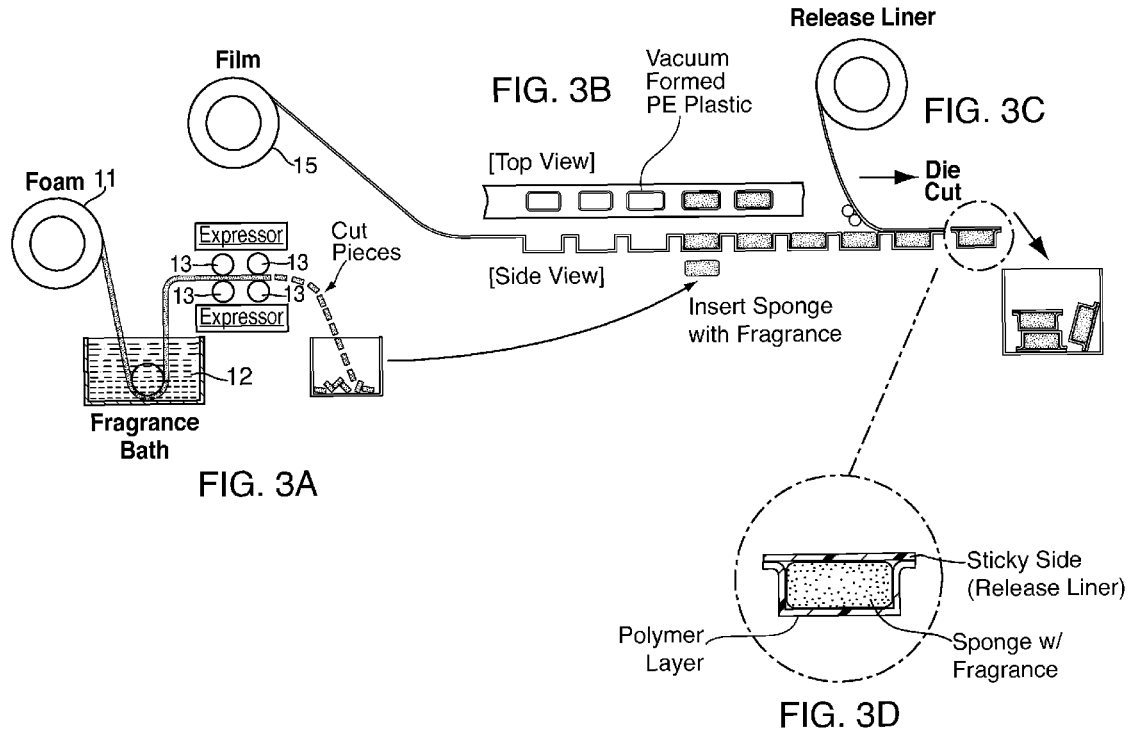

US 8,900,385 B2

COMPOSITE FOR ON DEMAND FRAGRANCE DELIVERY AND RELATED METHOD OF MANUFACTURE

This application claims the benefit of U.S. provisional application No. 61/337,704 filed Feb. 8, 2010, which is incorporated herein in its entirety by reference.

FIELD OF THE INVENTION

The present invention relates to a composite for on-demand fragrance delivery. In particular, the composite contains a top polymer layer, a middle foam layer containing fragrance and a bottom double sided film adhesive layer with release liner.

BACKGROUND OF THE INVENTION

The general disclosure of various open cell foams and foam composite materials are well known in the prior art. U.S. Pat. Nos. 6,617,014, 6,991,848 and 7,048,966 all to Thomson represent the state of the art in foam composite materials.

Further, foam materials with fragrance are also known. Representative patents include a foam coated with two layers of cationic polymers (SenGupta U.S. 2009/0162408); an open cell foam used in a respiratory protection device (McConnell U.S. Ser. No. 09/015,1728); an open cell foam substrate and bonded micro-packaged active ingredient particles (Hermann U.S. Pat. No. 5,098,621); a fragrance delivery system (U.S. Pat. No. 6,147,037 Gardlik); impregnated silica-silicate open cell foams with immiscible components (Foley U.S. Pat. No. 4,584,281); hydrophilic polyurethane foams with active materials incorporated into the cell structure thereof (Palinczar et al. U.S. Pat. No. 4,339,550); and a polyurethane foam containing a particulate filler and a fragrance material (Stone et al. U.S. Pat. No. 4,226,944)

Triplett (U.S. 2008/0279730) discloses a fragrance delivery system the specifically provided a multiple delivery vapor dispensing mechanism for on demand fragrance release.

U.S. Pat. No. 4,880,690 to Szycher et al. discloses a perfume patch comprising an ultra-thin polyurethane membrane and a pressure sensitive adhesive for adhering to the skin. The patch is essentially an impregnated foam with an adhesive layer designed to release fragrance for an extended period of time. There is no suggestion that the patch is encapsulated or that the fragrance is released on-demand.

U.S. Pat. No. 4,254,179 to Carson, III, et al. discloses a method for impregnating a porous foam product with a fragrance that is released over an extended period of time. Encapsulated fragrance beads are retained within the foam until they are broken to release the fragrance. The disclosure indicates a semi-pervious plastic film is adhered to the upper surface of the foam. Carson does not disclose a bottom adhesive layer, nor is there any disclosure discussing the release of fragrance by compression.

U.S. Pat. No. 6,736,335 to Cuthbert discloses a scent dispensing packet, has hollow cavity defined by outer resilient walls that retains desired scent, where packet is compressed to force scent through opening for delivering scent to user.

WO 02083043 discloses a fragrance emitting article used as sampling device for magazines, comprises support layer having upper surface dispersed with fragrance-containing microcapsules without binder, and lower surface disposed with adhesive.

U.S. Pat. Nos. 6,536,635 and 6,752,298 to Garcia et al. discloses a sample for dispensing liquid product such as perfume comprises elastic means increasing volume of reservoir when removable closure is removed.

U.S. Pat. No. 6,663,019 to Garcia et al. discloses a sample spray dispenser as a promotional aid comprising reservoir containing the fluid to be dispensed, a spray orifice, and actuating wall that can be deformed by applying a pressing force.

U.S. Pat. No. 7,815,878 to Wheatley discloses an air freshener device for providing desired scent, fragrance, aroma or neutralizing agent in e.g. vehicle, has flexible cover with fabric shell including inner liner to resist release of scent and scent material interspersed in foam body.

U.S. Pat. No. 7,682,575 to Hurwitz et al. discloses a scent dispersing mat apparatus for dispersing volatilized scent comprises perforated polymer cover sheet, flexible closed cell foam mat, and adhesive attachment mechanism; pressure applied to release fragrance.

U.S. Pat. No. 6,254,836 to Fry discloses a refillable hanging car air freshener contains apertures to carry scent from depressible bulb having an absorbent material containing a fragrance to surrounding area.

U.S. Patent Publication No. 2009/081912 to Burrow et al. discloses a fragrance emitting patch for delivering pleasing scent to user has primary porous layer provided with fragrance having Hildebrand solubility parameter which differs from Hildebrand solubility parameter of construction adhesive.

U.S. Pat. No. 4,257,176 to Hartung et al. discloses a deodorant insole for footwear having resilient cushion and resin coating with encapsulated volatile odor treating material.

U.S. Pat. No. 4,161,284 to Rattan discloses slow diffuser-air scent for vehicle—has absorbent pad recharged from reservoir by squeezing package sides having interior molded spines.

U.S. Pat. No. 4,858,831 to Spector discloses a hand-actuated fragrance emitting unit—has air filled container provided with small jet opening having flexible walls.

U.S. Pat. No. 4,254,179 to Carson III et al. discloses a fragrance impregnated foam—with microcapsules embedded in surface voids and covered with porous film (Column 1, Lines 40-65; Column 3, Lines 25-60).

EP 0525530 discloses a tightly-sealed, peelable perfume pouch label which includes a pressure sensitive adhesive back and a process for manufacturing such pouch label which facilitates its attachment to a magazine or other mailer. The pouch label (or pouch if no pressure-sensitive adhesive back is included) contains perfume which may be stored in a perfume-doped layer carried between two barrier members which prevent unwanted release or migration of fragrance or its oils. The top barrier member is peelably removable for sampling of the perfume stored within the pouch.

EP 1914269 discloses a porous material comprising 1. (a) an open-cell foam with a density in the range from 5 to 1,000 kg/m 3 and with an average pore diameter in the range from 1 μm to 1 mm, 2. (b) a storage system comprising 3. (c) a perfume. A storage system (b) in the context of the present invention can contain perfume (c) in finely dispersed form.

"Squeeze Mist" Emsar, www.emsargroup.com http://www.emsarproup.com/pdf/Squeeze%20Mist%20inch.pdf discloses an all-in-one mini spray package, consumers squeeze the plastic bottle to release a fine mist. Made of 98% polypropylene, the bottle is easy to squeeze and offers a quick return for multiple sprays.

Mecofoam by Prameco Co., Ltd http://www.ecplaza.net/product/108834__402063/perfumed_jewelry.html. Mecofoam is a metal material for jewelry and accessory, produced by specialized technology forming open cell-micro porosity inside of the metal so that it can absorb perfume or aroma oil and keep and give out fragrance continuously.

"DiscCover—Fine Fragrance" Arcade Marketing, 2011 http://www.arcadeinc.com/categories/technology/fine-fragrance/disccover.html dislcoses a perfume disposed between two scent impermeable sheets wherein the scent is released when the reclosable cover strip is lifted.

An article in MIT News Office (Jan. 27, 1999) discloses a microchip capable of storing and releasing different chemicals on demand. Tiny reservoirs built into the chips silicon structure are used to store the chemicals. The chemical inside is released with the application of a small electrical voltage to a given reservoir, and the thin gold cap covering it dissolves, thus releasing the chemical.

The invention overcomes these issues and problems by the providing a composite which includes a top polymer layer, a middle foam layer containing fragrance and a bottom double sided film adhesive layer with a release liner resulting in a polymer encased envelope to provide on-demand release of fragrance only when compressed.

Unlike the prior art, the invention provides a three-layered composite containing a top polymer layer, a middle foam layer imbibed with fragrance and a bottom double sided film adhesive layer with a release liner. Unlike any of the prior art references located, this polymer encased foam provides on-demand release of the fragrance only when compressed.

Accordingly, it is an object of the invention to provide a composite material for on demand release of fragrance.

A further object of the invention is to provide a fragrance "coupon" for use in a book to provide on-demand release of fragrance when compressed by the user.

A further object of the invention is to provide fragrance samplers, room fresheners and therapeutic treatments as in aroma therapy.

Yet still a further object of the invention is to provide a method for the production of a sample of a volatile chemical to test analytical equipment. A single compression of the device would release a known mass of a chemical to the atmosphere. This could be used to calibrate a gas chromatograph or similar device by the internal standards method.

SUMMARY OF THE INVENTION

In the present invention, these purposes, as well as others which will be apparent are achieved generally by providing a composite for on demand release of fragrance.

The composite of the invention includes a top polymer layer, a middle foam layer; and a bottom double sided film adhesive layer with a releaser liner on the outside surface; wherein said foam layer is imbibed with fragrance and released only when compressed.

The foam layer is preferably an open cell reticulated structure for holding the fragrance and is selected from the group consisting of polyurethanes and olefins. The material doesn't have to be a reticulated foam, but must be of a structure to retain the fragrance. Reticulated foams are generally 2% foam material and 98% air. The less foam membrane present in the composite, the higher the rate of transfer of fragrance.

The top polymer layer is preferably between 0.001 and 0.008 inches thick and virtually impermeable to the fragrance oil. The top layer is perforated with openings such that when the layers are compressed the void volume is quickly expelled and springs back in less than 1 second. The impermeable film material is preferably polyurethanes, PET, polypropylene or olefin material. In as much as the film is impermeable, perforations are needed to release the fragrance upon demand. In a preferred embodiment, the perforations are star shaped which open upon compression and expansion and then close at rest.

The bottom double-sided film adhesive layer is selected from the group consisting of polyurethanes and olefins. It is preferably between 0.001 and 0.01 inches thick and virtually impermeable to the fragrance oil. It is coated with a pressure sensitive adhesive having a silicone coated release liner on one surface. The release liner layer is preferably silicone or hydrocarbon-coated paper or plastic.

The invention also includes a method of making fragrance coupons as shown in FIG. 3. FIG. 3A shows immersing of a foam material 11 having a high melt index, in a bath of fragrance at ambient temperature or slightly below. The imbibed foam material is passed through at least one nip roller (expressor 13) to remove excess fragrance. The foam is then cut into desired pieces, preferably ¾ inch.

FIG. 3B illustrates the top film polymer layer, both side and top views. Essentially, cavities for the foam are created by vacuum and the foam immersed with fragrance is inserted into these cavities. FIG. 3 C illustrates the release liner which seals off the sponge in the respective cavity. The material is die cut to form the resulting composite material as shown in FIG. 3D.

The release liner can be removed to expose the sticky adhesive surface for use in a resulting product, preferably a book, wherein the fragrance is released upon demand by compression of the user.

Other objects, features and advantages of the present invention will be apparent when the detailed description of the preferred embodiments of the invention are considered with reference to the drawings, which should be construed in an illustrative and not limiting sense.

BRIEF DESCRIPTION OF THE DRAWINGS

FIG. 3 is a preferred illustration of the method and apparatus used to make the composite material of the invention.

DETAILED DESCRIPTION OF THE INVENTION

Figure 1:
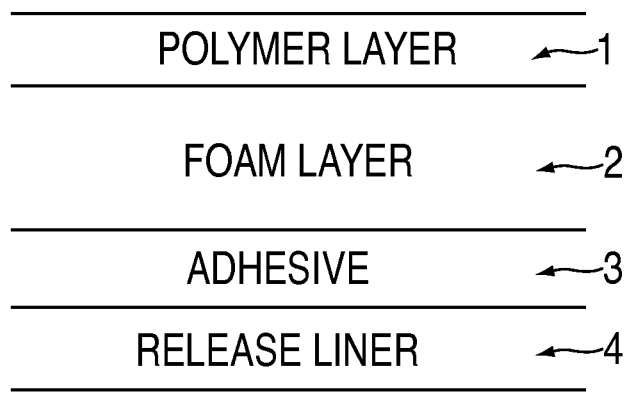
FIG. 1 is a cross-section of the composite material according to the invention.

In accordance with the present invention a composite for on demand release of fragrance is provided. As illustrated in FIG. 1, the laminate contains a top polymer layer 1, a middle foam layer 2 containing fragrance and a bottom double sided film adhesive layer 3 with release liner 4.

The resulting fragrance "coupon" is essentially foam imbibed with fragrance, encased in a polymer envelope to provide on-demand release of the fragrance only when compressed. Without compression no fragrance is released. In preferred applications these fragrance "coupons" are incorporated into books for use by readers.

The middle foam material used in the invention includes an open cell structure, possibly reticulated, for holding the fragrance oil or liquid. The foam has sufficient surface area to hold a given amount of fragrance oil such that no excess oil is allowed to drain. The foam can be a polyurethane, olefin or other material but there must be an affinity between the foam and the oil. The affinity is preferably dipole-dipole. The foam material is also resilient enough to return to its original dimensions within one second after compression is removed.

Although not limited to such, examples of foam material which may be used in the invention are found in U.S. Pat. Nos.

6,667,014, 6,991,848 and 7,048,966 all to Thomson. For essential oils whose vapor pressure is too low to give a sufficient odor experience adjuvents may be added.

The bottom film adhesive layer is selected from the group consisting of polyesters, polyurethanes and olefins. This layer has a sticky surface on both sides and has a release liner on one side. The sticky side of the adhesive layer adheres to the foam material. When ready for use, the release liner is removed to expose the other sticky surface and to provide easy adherence and positioning of the coupons within the resulting product, i.e. book. The release liner layer is preferably a silicone or hydrocarbon-coated paper or plastic.

The outer "top" polymer film is selected from the group consisting of polyurethanes and olefins. It is approximately 0.001 to 0.008 inches thick, preferably 0.002 inches. It is placed over the foam/adhesive tape such that the film extends on either side of the foam. The top layer material is generally impermeable but in the invention includes perforations to allow breathable to permit release of the fragrance smell upon compression but does not allow for evaporation of the fragrance. The invention coupons are designed for approximately 100,000 compressions before losing their smell.

Figure 2:
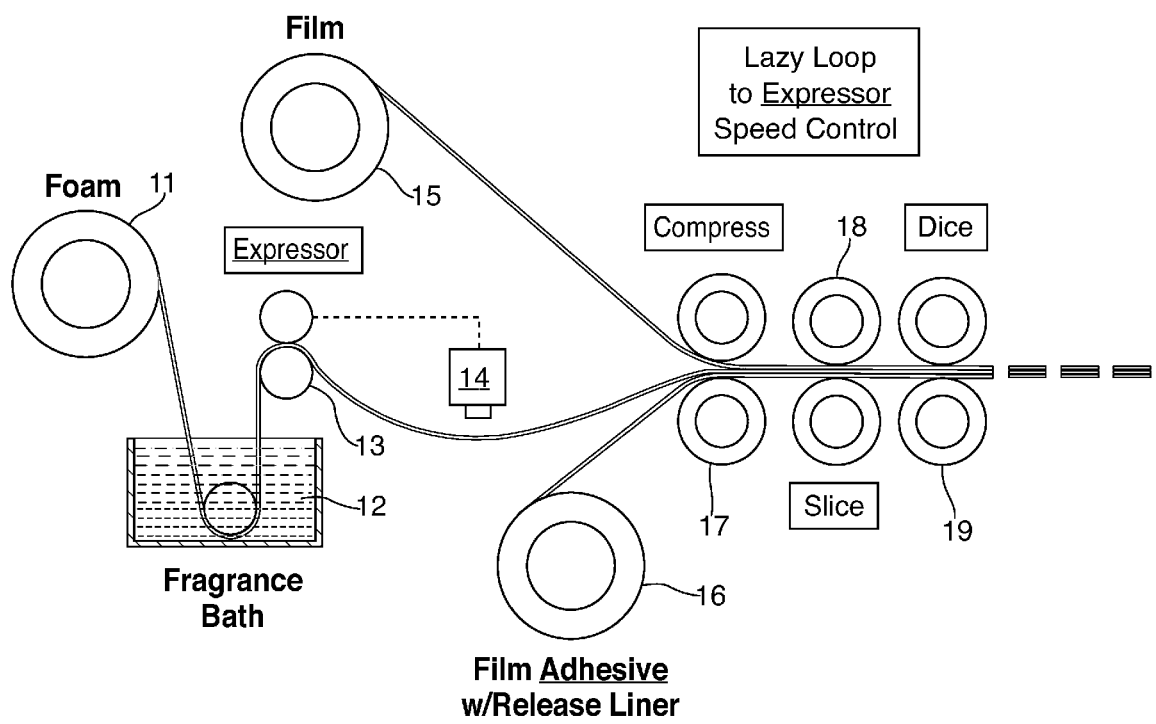
FIG. 2 is an illustration of the apparatus and method used to make the invention material.

The invention also includes the related method of manufacture of the fragrance coupons as illustrated in the attached FIG. 2. The foam 11 is immersed in a bath of fragrance 12 and, then run thru two closely spaced nip rollers 13 to remove the excess oil. The fragrance bath is preferably at ambient temperature or slightly below. The speed of the foam is controlled by a lazy loop control 14 arrangement in which the rate of take-up of the foam controls the speed of the oil-expressing rollers.

The polymer film 15 and the film adhesive with release liner 16 are simultaneously, along with the foam imbibed with fragrance, passed between nip rollers 17, 18, 19 to compress the three layers, thus encasing the foam. The edges of the material are cut off and parts are cut to length using an ultrasonic welder/cutter.

FIG. 3 illustrates an alternative embodiment in making the composite material of the invention. In general, cavities are vacuumed into the top film layer. The foam which has been impregnated with fragrance is placed within these cavities which are then sealed by the double sided (bottom) adhesive layer. These are die cut to produce the composite ("coupons") of the invention. Perforations in the top layer are made during the vacuum formation of the cavities.

More specifically, FIG. 3A shows immersing of a foam material 11 having a high melt index, in a bath of fragrance at ambient temperature or slightly below. The imbibed foam material is passed through at least one nip roller (expressor 13) to remove excess fragrance. The foam is then cut into desired pieces, preferably ¾ inch.

FIG. 3B illustrates the top film polymer layer, both side and top views. Essentially, cavities for the foam are created by vacuum and the foam immersed with fragrance is inserted into these cavities. FIG. 3 C illustrates the release liner which seals off the sponge in the respective cavity. The material is die cut to form the resulting composite material as shown in FIG. 3D.

The release liner can be removed to expose the sticky adhesive surface for use in the resulting product, i.e. book. In a preferred application, the release liner of the coupon is removed and the sticky adhesive surface is applied to the surface of a page of a book. Another sheet is applied over the page so, essentially the coupon is sandwiched between two sheets of paper or cardboard. The user compresses the desired spot to release the desired fragrance on demand.

The foregoing description of various and preferred embodiments of the present invention has been provided for purposes of illustration only, and it is understood that numerous modifications, variations and alterations may be made without departing from the scope and spirit of the invention as set forth in the following claims.

What is claimed is:

1. A method of making fragrance coupons comprising the steps of:
    immersing a foam material which is an open cell reticulated structure in a bath of fragrance, wherein said open reticulated structure holds the fragrance;
    passing said foam material thru at least one nip roller to remove excess fragrance;
    providing a top polymer layer wherein cavities are formed by vacuum in the top polymer layer; and a bottom film adhesive layer with release liner such that said foam material is placed within said cavities and sandwiched between said top layer and said film adhesive layer to form a laminate which is then die cut to the desired size to produce the coupon; wherein the coupon provides release of the fragrance only when compressed.

2. The method according to claim 1, wherein said foam is cut into pieces up to ¾" of an inch.

3. The method according to claim 1, wherein perforations are formed in the top polymer layer.

4. The method according to claim 1, wherein said bottom film adhesive layer is placed over said cavities sealing said foam material within.

5. The method according to claim 1, wherein the release liner of the coupon is removed and the bottom film adhesive layer is affixed to a desired surface.

6. The method according to claim 5, wherein the coupon is placed within two sheets of paper or cardboard.

\* \* \* \* \*